United States Patent [19] [11] Patent Number: 5,814,614
Kruck [45] Date of Patent: Sep. 29, 1998

[54] SUBSTITUTED GLUCOSE COMPOUNDS FOR TOXIC METAL ION REMOVAL FROM THE BODY

[76] Inventor: Theo P. A. Kruck, 46, Foxbar Road, Toronto, Ontario, Canada

[21] Appl. No.: 914,088

[22] Filed: Aug. 19, 1997

Related U.S. Application Data

[63] Continuation-in-part of Ser. No. 601,606, Feb. 14, 1996, abandoned.

[51] Int. Cl.[6] .................................................... A61K 31/70
[52] U.S. Cl. .............................................. 514/25; 536/17.3
[58] Field of Search ............................... 574/25; 530/17.3

[56] References Cited

PUBLICATIONS

Mao et al, Chemical Abstracts, vol. 100, #51933x, 1984.
Liu et al, Nucleosides & Nucleotides, vol. 14, pp. 1901–1904, 1995.

*Primary Examiner*—James H. Reamer

[57] ABSTRACT

According to the present invention, a pharmaceutical composition that comprises a compound which is a 2-deoxy-D-glucopyranose substituted in the 2 position and is of the general formula (I):

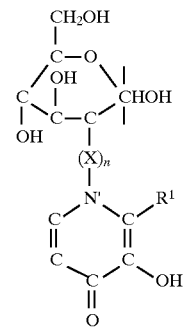

where $x_n$ is —NHCO(CH$_2$)$_m$ CHR$^2$— and m and n are 0 or 1; and R$^1$ is selected from methyl or ethyl, and R$^2$ is hydrogen or a substituent group selected from CH$_3$—, (CH$_3$)$_2$CH—, (CH$_3$)$_2$CHCH$_2$—, CH$_3$CH$_2$CH(CH$_3$)—, CH$_3$SCH$_2$CH$_2$—, C$_6$H$_5$—CH$_2$—, HOCH$_2$—, CH$_3$CH(OH)—, HSCH$_2$—, HO—C$_6$H$_4$—CH$_2$—, H$_2$NCOCH$_2$—, H$_2$NCOCH$_2$CH$_2$—, HOCOCH$_2$—, HOCOCH$_2$CH$_2$—, H$_2$NCH$_2$CH$_2$CH$_2$CH$_2$—, H$_2$NC(NH)NHCH$_2$CH$_2$CH$_2$—,

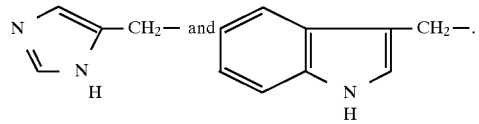

or a physiologically acceptable salt thereof. The pharmaceutical compositions are useful in the treatment of metal intoxication where the metal is selected from ionized iron or aluminum.

19 Claims, No Drawings

SUBSTITUTED GLUCOSE COMPOUNDS FOR TOXIC METAL ION REMOVAL FROM THE BODY

This is a continuation in part application of Ser. No. 08/601,606, filed Feb. 14th 1996 now abandoned.

FIELD OF INVENTION

The present invention relates to hydroxypyridone glucose derivatives for use in pharmaceutical compositions for treating toxic metal overload, especially focal concentrations of ionized aluminum or iron.

BACKGROUND TO THE INVENTION

Certain pathological conditions are consequences of un-natural deposits of metals such as iron or aluminum at levels toxic to the body. For example thalassaemia, sickle cell anemia, idiopathic haemochromatosis, aplastic anemia are conditions treated by regular blood transfusions, which frequently lead to iron overload and generally results in saturation of ferritin and transferrin with the excess iron depositing in other body compartments or tissues. This results in toxic effects leading to degeneration of tissues, especially myocardium, liver, endocrine organs and brain. The preferred treatment is by iron chelation utilizing the trivalent metal chelation drug deferoxamine-mesylate, commonly referred to as "DFO".

Certain forms of osteomalacia and dialysis encephalopathy syndrome (DES) show high levels of aluminum in bone or raised levels in brain and in the circulatory system. Reports indicate that DFO treatment of DES patients reduces blood aluminum levels and can reverse the encephalopathy condition. Accumulations of toxic amounts of aluminum, with or without excess loosely bound iron occur in brain of Alzheimer's disease (AD) patients. A link has been established between an increased risk for developing sporadic Alzheimer's disease and increased levels of residual aluminum in drinking water (1, 2).

Further, in a clinical treatment trial where AD patients were treated with DFO chelation, 125 mg DFO twice a day, 5 days a week for 24 months by intramuscular injection, it was demonstrated that the rate of deterioration could be reduced by 50% over a 24 months period (3).

DFO is a natural product obtained by a fermentation process from cultures of a streptomyces strain and is costly to produce. Since, the chelation treatments may go on for prolonged periods of time, 24 months for the AD treatment and since, DFO being susceptible to degradation by stomach acid cannot be given orally without causing stomach upset and severe pain and consequently must be administered systemically, by injection or infusion and since, some individuals subjected to chronic DFO treatment develop noxious side effects (4), it is highly desirable to provide cheaper, orally active, alternate pharmaceutical compounds and compositions for treatment of these deadly disease conditions.

Extensive research has been directed towards the development of alternate drugs for the treatment of iron intoxication (5–10). Several classes of compounds were investigated as iron chelating agents. Siderophores, namely hydroxamates are acid labile and offer no advantage over DFO and compounds such as ethylenediaminetetra-acetic acid (EDTA) and analogues and catechols are ineffective in removing intra-cellular iron. In addition catechol and its derivatives are retained by the liver and spleen while EDTA and analogues have associated high affinity for calcium likely to cause toxic problems at the necessary therapeutic concentrations.

Exploiting the fact that molecules containing an alpha-hydroxy ketone group form good iron and transition metal chelators, Hider et. al. synthesized a series of compounds based upon polysubstituted 3-hydroxypyrid-2-ones and 3-hydroxypyrid-4-ones, which contain the desired alpha-hydroxy ketone group within the pyridine ring structure, carying a variety of substituent groups said to control hydrophobicity of the molecules which, in turn, as it was claimed, controls solubility and availability for uptake into the blood stream (11–14). These compounds were claimed to be useful in iron chelation and are included in a series of patents by Hider et. al. (11–14), constituting instant art and thus, these compounds are excluded from this invention.

In this series, 1,2 dimethyl-3-hydroxypyrid-4-one, also called "L1" or "Deferriprone" was the preferred compound for pharmaceutical application and tested in human and rat for urinary iron excretion (7). In short term clinical trials involving young thalassaemia patients, it was demonstrated that treatment with this compound to remove iron from the body was effective. However, metabolic conversion generates toxic metabolites and renders the compound toxic at all levels, thus putting into question its usefulness, especially in long term treatment strategies. At this instant, it is not known whether any of the other compounds cited in the Hider et al patents (10–14), are toxic or non-toxic at physiological levels.

In addition, Hider et. al. describe the synthesis and use of selected 3-hydroxypyrid-4-ones (15) and thus form instant art and are excluded from the present invention. These latter compounds are claimed to be useful for the treatment of iron overload in blood and other extracellular fluids which would include removal from sites in direct contact with blood or other extra cellular fluids. However, no clinical data are available. Further, it is theorized that these compounds "are also of potential interest for the removal of other metals present in the body in deleterious amounts, for example copper, plutonium and other transuranic metals, and aluminum".

The above disclosure in U.S. Pat. No. 5,480,894, Jan. 2, 1996, (15) further informs us, that it is of importance that "selection of a particularly suitable chelating agent for the oral treatment of iron overload presents two contradictory requirements as far as it is desirable that the agent used' is efficient at entering the bloodstream' and thus the liver from the gastrointestinal tract and secondly that it is not efficient at crossing the blood brain barrier". Thus, the thrust of the invention disclosed in said Patent is the creation of compounds that favour entry into the bloodstream through addition of hydrophobic residues which can be cleaved off by liver enzymes producing compounds which would still chelate iron but would not cross the blood brain barrier. It states further, that "2-{alpha-methylproprionyloxy}ethyl or 2-pivaloyloxyethyl substituted 3-hydroxypyrid-4-one compounds will get metabolized by the liver enzymes to 1-hydroxyethyl-substituted-pyridin-4-ones, which are not efficient at crossing the blood brain barrier." It further states, that preferred embodiments of chelators for medical use should not cross the blood brain barrier (14). Again, this emphasizes an importance, that is preference, to keep these chelation compounds from crossing the blood brain barrier.

Furthermore, Christensen et. al., in U.S. Pat. No. 5,514, 668, May 7, 1996, (15) claim and teach that attachment of functional 'crownether' compounds to polysaccharide molecules, preferably of molecular weight between 1,000 and 120,000, will both, render the crownethers soluble in body fluids, such as blood, and will prevent their insertion into cellular membranes or intra-cellular space, which is commonly thought to produce the toxic effects. The compositions presented are not identified as being orally active but, it is stated that "the composition shall be administered intravenously". It teaches further, that polysaccharide, especially dextran, incorporation imparts excretability by the kidney function to such compounds. It is further stated as theoretical possibility that, "The composition (crownether-dextran adducts) is also suitable for treating poisoning by binding and preferably removing ions of e.g. the following metals: Pb, Ag, Hg, Au, Cd, Cu, Zn, Na, K as well as radioactive Cs"; aluminum is not included. Thus, Christensen et. al. (15) does not guide us to select or synthesize compositions which are orally active, are taken up into the bloodstream after ingestion, will cross the blood brain barrier, cytoplasmic membranes and penetrate specific intracellular spaces, such as neuronal nuclei where toxic amounts of aluminum can accumulate, as it is found in focal regions of the Alzheimer's diseased brain (16).

Contrary to the above stated preferences claimed by Hider et. al. (14) and Christensen et. al. (15), for treatment of the sporadic form of Alzheimer's disease, where the toxic metal aluminum is deposited on specific intracellular target sites (3, 16), it is of importance, that the preferred chelating compound crosses the blood brain barrier and is able to cross the cytoplasmic membranes of neuronal cells in the brain, whose destruction is involved in generating the Alzheimer's syndrome.

Hostetler et al. (17) showed that absorption of a number of specific drugs that are not readily absorbed by the gastro-intestinal tract, can be enhanced by coupling them to a class of lipid molecules generally recognized as 1-O-alkyl, 1-O-acyl, 1-S-acyl and 1-S-alkyl-sn-glycero-3-phosphates. Some of these combination molecules can cross cytoplasmic membranes, however, the instant knowledge flowing from this work is not informative as to the utility of attaching iron or aluminum or general metal chelators to such lipophosphate residues in order to generate orally active, nontoxic compositions for treatment of specific metal toxicity related disorders. Especially, it is not known if such compounds would cross the blood brain barrier to deliver sufficient amounts of chelator activity to achieve effective metal removal.

Porter et al (18), studying iron mobilization from hepatocytes in tissue culture by various chelators found that membrane permeability and the stability constant of each species exerted controlling effects upon the removal process. This teaches us that transport of the chelating molecule across cell membranes and the ability of the metal, specifically the iron-chelate to exit the cellular cytoplasm, in addition to the relative strength, the stability constant, of the chelate bonds, will control the metal removal process.

This important observation on iron chelation and transport was tested for aluminum on isolated human neuronal nuclei from AD brain (19). Nuclei in appropriate physiological buffer were exposed for a predetermined time to DFO, the drug of choice, used in the clinical trial, for treating sporadic AD (3) and the amount of aluminum liberated by chelation was found to be in the order of 10%. Ascorbic acid a natural iron and aluminum chelator in this system released 20%. An adjunct treatment utilizing DFO together with ascorbic acid under the same conditions liberated 30–35% of total nuclear aluminum (19). It is important to note that both, ascorbate and DFO are sufficiently water soluble and in aqueous systems the affinity of DFO for aluminum is higher than that of ascorbate. In this instance DFO, being the larger molecule, is excluded form penetrating sufficiently the intra-nuclear structures, such as chromatin, from which aluminum must be removed, ascorbate being a smaller molecule can reach the remote aluminum binding sites more readily.

This knowledge teaches us that the mechanism of aluminum removal is complex and that the ability of a compound to chelate aluminum in biological systems is not predictable from solubility and stability constant criteria alone. Diffusion and active transport mechanisms regulating traffic across membrane systems assume paramount significance. This is exemplified by glucose transport into cells having high metabolic energy requirements such as muscle and especially brain cells. Thus, incorporating a glucose residue in drug compounds may be useful in targeting brain tissue which is an aim of the invention.

It is highly desirable that compounds be created which, in addition to entering the bloodstream from the gastrointestinal tract and crossing the blood brain barrier, can enter intracellular compartments, bind the toxic metal deposits comprising aluminum ions with high enough affinity, exit the cell, enter the circulatory and excretory systems to be rendered harmless by excretion from the body. To satisfy the complex requirements of aluminum removal from intracellular sites especially the nuclear compartment, which is an essential step in the treatment of sporadic AD, I have grafted aluminum chelating residues consisting of substituted 3-hydroxypyrid-4-ones onto a D-glucose molecule to generate novel compounds which are particularly useful for incorporation into medicines for the removal of aluminum and loosely bound iron from brain, of humans suffering from the effects of aluminum intoxication or especially from the sporadic form of AD.

REFERENCE LIST

The present specification refers to the following publications, each of which is expressly incorporated herein by reference.

1. T. P. A. Kruck, "Alzheimer-aluminum link", Nature 1993; 363: 119.

2. D. R. C. McLachlan et. al., "Risk for neuropathologically confirmed Alzheimer's disease and residual aluminum in municipal drinking water employing weighted residual histories", Neurology, 1996; 46: 401–405.

3. Crapper McLachlan et al., "Intramuscular Desferrioxamine in Patients with Alzheimer's Disease.", The Lancet 1991; 337: 1304–1308.

4. T. P. A. Kruck et al., "Suppression of Deferoxamine-mesylate Treatment Induced Side Effects by Co-administration of Isoniazid in a Patient with Alzheimer's Disease Subject to Aluminum Removal by Ionspecific Chelation", Clinical Pharmacology and Therapeutics 1990;48:439–446.

5. C. G. Pitt et al., "The Design and Synthesis of Chelating Agents for Treatment of Iron Overload in Colley's Anemia", Research Triangle Institute, DHEW Publication No. 77-994, 1975.

6. B. Tamhina et al., "Extraction and Spectrophotometric Determination of Iron (III) by 1-Phenyl-2-Methyl-3-Hydroxy-4-pyridone", Croatia Chemica Acta CCACAA 1973; 45 (4): 603–610.

7. S. Singh et. al. "Urinary metabolic profiles in human and rat of 1,2-dimethyl-substituted 3-hydroxypyridin-4-ones", Drug. Met. and Disp., 1992; 519: 171–178.

8. C. M. Brady et. al. "Release of iron from ferritin molecules and their iron-cores by 3-hydroxypyridinone chelators in vitro", Journal of Inorganic Biochemistry, 1989; 35: 9–32.

9. Jacobs, "Screening for Iron Chelating Drugs", Elsevier North Holland, Inc., 1981; pp. 39–46.

10. G. J. Kontoghiorghes, "Comparative efficacy and toxicity of desferrioxamine, deferiprone and other iron and aluminum chelating drugs". Toxicology letters, 1995; 80: 1–18.

11. R. C. Hider et. al., "Pharmaceutical compositions", U.S. Pat. No. 4,585,780, Apr. 29, 1986.

12. R. C. Hider et. al., "Iron-Pyridone complexes for anemia", U.S. Pat. No. 4,650,793, Mar. 17, 1987.

13. R. C. Hider et. al., "3-Hydroxy-pyridin-4-ones useful for treating parasitic infections", U.S. Pat. No. 5,256,676, Oct. 26, 1993.

14. R. C. Hider et. al., "3-hydroxypyridin-4-one derivatives as chelating agents", U.S. Pat. No. 5,480,894, Jan. 2, 1996.

15. H. M. Christensen et.al., "Composition for removing or inactivating harmful components in blood or other extra-cellular body fluids", U.S. Pat. No. 5,514,668, May 7, 1996.

16. T. P. A. Kruck et. al., "Aluminum as a Pathogenic Agent in Alzheimer's Disease", Legal and Ethical Issues in Alzheimer's Disease Research, J. M. Berg, H. Karlinsky and F. Lowy (eds.), 1991, Gage Educational Press, Toronto.

17. K. Y. Hostetler et. al., "Method of converting a drug to an orally available form by covalently bonding a lipid to the drug", U.S. Pat. 5,411,947, May 2, 1995.

18. Porter et. al., "Iron mobilization from hepatocyte monolayer cultures by chelators: the importance of membrane permeability and the iron binding constant", Blood, 1989; 72: 1497–1503.

19. Kruck, T. P. A., Crapper McLachlan, D. R., Bergeron, C. and Lukiw, W. J. Aluminum in Neocortical Nuclei - Removal by Shuttle Chelation and Relevance to Alzheimer's Disease. In: Alzheimers Disease an Related Disorders, Advances in the Biosciences Vol. 87, M. Nicolini, P. F. Zatta and B. Corrain eds. (1993) Pergamon Press.

SUMMARY OF INVENTION

It is an object of the invention to provide a therapeutic agent and medicine, especially for the treatment of aluminum or iron overload and, the treatment of patients suffering from sporadic Alheimer's disease.

A further object is to provide pharmaceutical compositions that are effective when administered by mouth and are essentially safe, and free from noxious side effects when applied at physiologically active concentrations.

The unique embodiment of the invention is achieved by joining chemically precursor compounds derived preferably from natural sources, such as maltol, ethyl maltol, amino acids and other natural substances. The chelating compounds comprised by the invention are generated by chemically joining a maltol molecule, which carries the alpha-hydroxy ketone chelation group, either directly to a glucose molecule or joining the maltol group through an amino acid linker molecule, preferably glycine or beta alanine, to the glucose molecule. Included in this invention are compositions that show differing activities based upon differing spacial distribution but having same stoichiometry of atoms of the compound, as it may be expressed through optical activities, such as L and D or R and S configurations.

The present invention comprises compounds consisting of a modified glucose molecule having attached to it either a 3-hydroxy-2-alkyl-pyridin-4-one or an amino acid which has attached to it a 3-hydroxy-2-alkyl-pyridin-4-one group where the alkyl group is preferably selected from ethyl or methyl groups. The invention further encompasses compositions comprising the compounds, 3-hydroxy-2-alkyl-pyridine-4-one substituted D-glucose, optionally being in the form of a physiologically acceptable salt, mixed with physiologically acceptable carrier suitable for pharmaceutical applications. The invention also relates to the use of those compounds in pharmaceutical compositions as medicine for treating toxic metal overload, especially focal concentrations of ionized aluminum as it is found in certain forms of Alzheimer's disease, or iron as it may be found in iron intoxication.

Compositions useful for oral treatment of aluminum intoxication as defined herein for neurological disorders include incorporation of the active chelator 100–1000 mg mixed with binder and carrier substances and shaped and pressed into tablets, or mixed with inert fillers and filled into pharmaceutically approved, preferably gelatine, capsules (chaplets). A preferred tablet mixture contains 500 mg, or a lesser unit dose of active chelator, selected from 2-substituted -2-D-deoxy-glucopyranose compounds especially: 2-deoxy-2-[N'-2'-methyl-3'-hydroxypyrid-4'-one]-D-glucopyranose, 2-deoxy-2[N'-2'-ethyl-3'-hydroxypyrid-4'-one]-D-glucopyranose, 2-deoxy-2-(N-carbamoylmethyl-[N'-2'-methyl-3'-hydroxypyrid-4'-one])-D-glucopyranose, 2-deoxy-2-(N-carbamoylmethyl-[N'-2'-ethyl-3'-hydroxypyrid-4'-one])-D-glucopyranose, 2-deoxy-2-(N-carbamoylethyl-[N'-2'-methyl-3'-hydroxypyrid-4'-one])-D-glucopyranose.

According to the present invention, a pharmaceutical composition comprising a compound which is a 2-deoxy-D-glucopyranose substituted in the 2 position and is of the general formula (I):

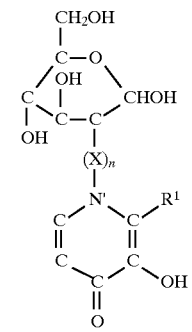

where $x_n$ is —NHCO(CH$_2$)$_m$CHR$^2$— and m and n are 0 or 1; and R$^1$ is selected from methyl or ethyl, and R$^2$ is selected from hydrogen, CH$_3$—, (CH$_3$)$_2$CH—, (CH$_3$)$_2$CHCH$_2$—, CH$_3$CH$_2$CH(CH$_3$)—, CH$_3$SCH$_2$CH$_2$—, C$_6$H$_5$—CH$_2$—, HOCH$_2$—, CH$_3$CH(OH)—, HSCH$_2$—, HO—C$_6$H$_4$—CH$_2$—, H$_2$NCOCH$_2$—, H$_2$NCOCH$_2$CH$_2$—, HOCOCH$_2$—, HOCOCH$_2$CH$_2$—, H$_2$NCH$_2$CH$_2$CH$_2$CH$_2$—, H$_2$NC(NH)NHCH$_2$CH$_2$CH$_2$—,

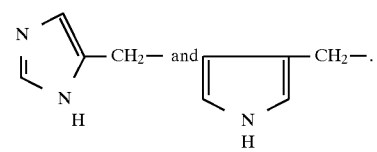

or a physiologically acceptable salt thereof and optionally the compound being mixed with physiologically compatible diluents or carrier substances suitable for formulating medicines which may be in the form of tablets, capsules, slurry, powder, solution, or incorporation into patches or any other form that is convenient for effective oral, rectal, transcutaneous or systemic administration and if pharmacologically advantageous may have added additional pharmacologically active compounds that enhance the effectiveness of the compounds in the invention. The ability of the compounds and their metal complexes to permeate membranes and cross biological barriers is important in the context of iron or aluminum overload, especially, in the case of aluminum removal from the body, it is desirable that the compound crosses biologically active membranes, which is not critical in iron removal from the blood circulation. To be useful for aluminum removal, it is desirable that the compound does not only possesses both water and lipid solubility but also possess substituent groups which can mimic natural substances for which, in the body, the cells of interest have specific transport systems or mechanisms, for example the glucose transport system in high energy requiring neurons, which can facilitate membrane transport.

Solubility is governed by the presence of particular substituent groups, that are polarizable, ionizable or hydrophobic in character and which are present in the 3-hydroxypyrid-4-one substituted D-glucopyranosyl compounds of the invention. Of special importance is the D-glucose residue which can facilitate transport across cellular membranes by utilizing the glucose transport system.

Also of considerable interest is that neurons, important target cells in aluminum intoxication have high energy, glucose requirements and an active glucose transport system which permits preferential targeting of the chelating compounds of the invention to the cells where chelation of toxic levels of metal such as aluminum is required.

It should be noted, that through lack of precise knowledge of the mechanism by which Alzheimer's disease is generated, it was difficult to select appropriate chelating compounds to develop a treatment strategy. A critical step in the development of sporadic, or late onset Alzheimer's disease appears to be deposition of high concentrations of aluminum in focal areas of the brain and especially in the nucleus of neuronal cells. Therefore, it is desirable that the chelating agent once in the blood circulation be able to cross the blood brain barrier and cellular membranes to reach remote intranuclear compartments, where aluminum which in such locations can interfere with functions necessary for cellular "housekeeping" and survival, leading to apoptosis (programmed cell death), and chelate the offending aluminum ions, exit the nucleus, the cellular compartment, enter the blood stream, and preferably be eliminated via the urinary (kidney) system. Most importantly, the chelator must bind aluminum in such a manner that it cannot be re-deposited in other organs.

Thus, selection of a suitable chelator for the oral treatment presents several challenges. The trivalent metal chelating drug DFO is able to remove brain aluminum and efficiently excrete it through the kidney system (3). However, aluminum removal efficiency of DFO is low because of its quite limited ability to cross the blood brain barrier and penetrate the nuclear compartment.

In contrast, compounds of the invention as defined in the general formula especially useful and preferred for formulating into pharmaceutical compositions or medicines to treat aluminum intoxication are selected as follows:

A preferred compound being according to formula (I), wherein m=0, n=0 and $R^1$ is a methyl group, 2-deoxy-2-[N'-2'-methyl-3'-hydroxypyrid-4'-one]-D-glucopyranose. Or a compound being according to formula (I), wherein m=0, n=0 and $R^1$ is an ethyl group, 2-deoxy-2-[N'-2'-ethyl-3'-hydroxypyrid-$4^1$-one]-D-glucopyranose. Or a compound being according to formula (I), wherein m=0, n=1 and $R^1$ is a methyl group and $R^2$ is hydrogen, 2-deoxy-2-(N-carbamoylmethyl-[N'-2'-methyl-3'-hydroxypyrid-4'-one])-D-glucopyranose. Or a compound being according to formula (I), wherein m=0, n=1 and $R^1$ is an ethyl group and $R^2$ is hydrogen, 2-deoxy-2-(N-carbamoylmethyl-[N'-2'-ethyl-3'-hydroxypyrid-4'-one])-D-glucopyranose. Or a compound being according to formula (I), wherein m=1, n=1 and $R^1$ is a methyl group and $R^2$ is hydrogen, 2-deoxy-2-(N-carbamoylethyl-[N-2'-ethyl-3'-hydroxypyrid-4'-one])-D-glucopyranose. These compounds can cross membranes by virtue of a) their mixed hydrophobic/hydrophillic structure and b) a facilitated transport associated with the glucose residues of the compounds of interest. In general terms, compositions of most interest are limited to those that are generated by combination of naturally occurring substances, selected from 'maltol, ethyl maltol, amino acids and amino sugars', including alcohols and other natural substances and standard, commonly known reagents used in organic synthesis. Included in this invention are compounds that show differing activities based upon differing spacial distribution (same stoichiometry) of atoms as it is expressed through L and D or R and S configurations. This selection of specific starting compounds is important for providing pharmaceutical compositions that are free from toxic side effects and possess properties that are advantageous for transmembrane transport which is important for their specific biological activity. The present design of specific chelation compositions of value is novel and the compounds are not obvious. One must appreciate and judge possible metabolic reactions to arrive at suitable nontoxic composition.

Compounds included in this invention may be readily synthesized in several ways by practitioners in the field. It is understood that workers in this field can execute easily all the necessary chemical reactions, while it is also recognised that there are other routes to prepare the above mentioned intermediate or final compounds.

The substituted glucose compound may be conveniently prepared by reacting an aliphatic amine, $RNH_2$, which may be an amino acid or an amino sugar such as glucosamine, in the presence of a base which may be an alkali metal hydroxide such as sodium hydroxide, directly with the appropriately substituted 2-alkyl-3-hydroxypyrid-4-one, where the substituent alkyl group is selected from ethyl or methyl (group). The R-group in the amine is the desired R-substituent, or can be obtained by conversion to the R-group of an R'-substituent that contains modifiable groups such as an ester group, for example, which can be hydrolysed to yield the desired carboxylate. In particular, in this invention, the organic amines selected for reaction with the substituted 2-alkyl-3-hydroxypyrid-4-ones, where the alkyl group is selected from ethyl or methyl, are selected from the naturally occurring, commonly known amino acids, in particular their alkali metal salts, sodium being preferred, or amino sugars, D-glucosamine in particular. Additional modification of the amino acid prothetic group is achieved conveniently by a peptide bond or ester bond formation, utilizing known procedures, between the carboxyl group of the amino acid and the amino group of the modifying substituent moiety, preferably an un-substituted or substituted amino sugar.

For example, a particular N-substituted 2-alkyl-3-hydroxypyrid-4-one intermediate may be produced by reacting an amino acid such as the sodium salt of glycine or beta-alanine with 3-hydroxy-2-methylpyrid-4-one in the presence of alkali metal hydroxide, preferably sodium hydroxide. Alternatively, ethyl or methyl esters of glycine may be reacted in the presence of low concentrations of alkali metal hydroxide, sodium hydroxide being preferred, employing appropriate amounts of ethanol or methanol in the solvent to yield the ethyl or methyl ester protected compound. The esters can be hydrolysed under standard alkali or acid hydrolysis conditions to yield the free carboxyl group, which can be reacted with the amino group of the desired prosthetic group, utilizing the dicyclohexylcarbodiimide (DCC) coupling method, with dimethyl formamide as solvent, to avoid ester formation with hydroxy groups of the glycosidic moiety, these hydroxy groups may be esterified with acetate or other aliphatic carboxylic acids prior to the DCC promoted peptide coupling and followed by acid or base hydrolysis of the ester groups. Alternately, employing N-hydroxysuccinimide and DCC the carboxy group can be converted into the active N-succinimide ester which may be reacted with glucosamine having attached appropriate protecting groups having the (sugar) amino group of glucosamine free.

It must be appreciated that because of the ionizable nature of the compounds useful in metal coordination, the final composition may involve ion pair formation, protonation or deprotonation, complexation with inorganic or organic acids. The compounds of interest all have the pyridine nitrogen which can accommodate a proton to yield a positively charged compound that will have the anionic residue of the acid which donated the proton, coordinated as an ion pair. Such 'salt' formation will alter the solubility in aqueous or hydrophobic solvents and will be of value in design of the final composition.

Further, trivalent metal coordination, where metal is represented by aluminum or iron, will involve bidentate attachment involving coordination bonds between the metal ion, the 4-position carbonyl and the 3-position hydroxy group, where upon metal coordination the proton on the hydroxyl group will be displaced making way for the oxygen-metal ion bond. The liberated hydrogen ion must be neutralized by an anion present in or added to the system in order to maintain the Ph of the solvent medium. This applies in vitro but has equal consequences in vivo. Also, the composition may vary according to the nature of the solvating medium. Factors such as Ph, salt concentration or hydrophobicity may control the presence of anions or cations or both simultaneously and will influence the final composition. However, given the same physical or physiological conditions the composition will be uniquely the same, thus, these various compositions are part of the present invention.

It should be noted that at neutral Ph, both iron and aluminum form 3:1 ligand:metal complexes, where the ligand is a molecule comprising the alpha-hydroxy-ketone group of the 3-hydroxypyrid-4-one and the various substituent groups as represented by the samples of this invention. The various iron complexes will show a light absorption in the visible range, approximately 450–550 nm, to the eye this appears as a red-purple to blue-purple colour either in solution or as bands on Thin-layer chromatography (TLC) plates. Aluminum forms similar 3:1 ligand:aluminum complexes which, however, do not show an absorption in the visible band. Nevertheless, the aluminum ligand complexes can be reacted with ionic iron which will displace the aluminum and form the coloured iron-ligand complex thus, iron can act as a surrogate reporter for the presence of such complexes.

The primary use of the compounds is in pharmaceutical formulations for treatment of human or animal medical conditions. The compounds may be formulated as aqueous or oily liquid or emulsion for systemic administration such as intramuscular-, subcutaneous-, intraperitoneal injection, or parenteral administration and consequently will be sterile an pyrogen free. However, it is most useful to formulate the compositions for oral administration. In this case the formulation may be a liquid or a solid, with the latter being preferred, because of the ease of delivering exact doses of the compound. The liquid carrier may be water containing modifying physiologically acceptable ions, aiding in solubilization, or a lipid or oil containing emulsion ensuring homogeneous distribution of the compound. As a solid formulation the composition may contain conventional carrier material such as starch, sugars, dextrin, cyclodextrin, soaps, such as zinc stearate and salts and binders in addition to the compound, which is measured in unit doses and may be formed into tablets or packed into capsules.

The active compound may be present also in multiple or submultiple doses. However, the preferred dosage will be determined by the efficiency of the particular compound in iron or aluminum sequestration, although, upper limits are imposed by potential toxicity considerations. Previous experience with DFO-chelation suggests that daily doses of the compounds in the invention between 0.1 g and 2 g may be sufficient to attain high enough levels in blood for control of iron in the human body. It will be appreciated that different pathological conditions require different dosage, which may be more or less than the suggested amounts. Also, since the aluminum-chelate stability is less than that for iron, different dosing both in quantity and frequency of gavaging may be of use and is controlled by the pathological condition to be treated.

Of particular importance is, that DFO, which is a proven chelator cannot be given orally, but needs to be administered systemically by injection (3). Among the substituted 3-hydroxypyrid-4-ones given by previous art, the compound 1,2-dimethyl-3-hydroxypyrid-4-one also called 'L1', as a trivial name, was found to be most useful and was tested on humans. Under physiological conditions of pH and salt concentration, it has a higher affinity constant for iron binding than transferrin, forms 3:1 ligand-iron complexes which are eliminated by kidney filtration. Similar to DFO it has low affinity for calcium which is an essential, critical body component. However, 1,2-dimethyl-3-hydroxypyrid-4-one was in clinical trials found to be toxic at all concentrations, therefore it is highly desirable to produce compounds with comparable metal binding ability, but without the attendant toxic effects of 'L1'. In contrast, the compounds in this invention will not produce toxic side effects because precautions are taken not to introduce into the compounds any substituents which may be metabolized into toxic products.

Even though, compounds in this invention may be of value in treating certain animal pathological conditions, they are especially useful to treat a variety of human conditions. Iron overload conditions associated with beta-thalassaemia are beneficially treated by iron-chelators such as DFO or chelators described herein.

The chelators described herein are also of interest in treating other less well known disease conditions associated with iron or aluminum toxicity. Thus, the present invention includes the use of selected, 2-substituted -2-D-deoxyglucopyranose compounds especially 2-deoxy-2-[N'-2'-methyl-3'-hydroxypyrid-4'-one]-D-glucopyranose, 2-deoxy-2-[N'-2'-ethyl-3'-hydroxypyrid-4'-one]-D-glucopyranose, 2-deoxy-2-(N-carbamoylmethyl-[N'-2'-methyl-3'-hydroxypyrid-4'-one])-D-glucopyranose, 2-deoxy-2-(N-carbamoylmethyl-[N'-2'-ethyl-3'-hydroxypyrid-4'-one])-D- glucopyranose, 2-deoxy-2-(N-carbamoylethyl-[N'-2'-methyl-3'-hydroxypyrid-4'-one])-D-glucopyranose, or salt complexes thereof as described herein, as medicine, for example, to remove toxic amounts of metal from the body especially aluminum and most importantly aluminum located in the nuclear confines of neuronal brain cells, iron and other trivalent metals less important to this invention. The invention also includes a method for treatment of patients having toxic amounts of metal in the body or in certain body compartments which comprises administration to the patient of certain amounts of 3-hydroxypyrid-4-one substituted D-glucopyranose compounds as described hereinbefore to effect reduction of the toxic levels of the metal in the body of the patient. The compounds of this invention are useful in the treatment of aluminum intoxication which is found frequently with renally impaired patients, including renal dialysis where aluminum overload in the blood may lead to dialysis encephalopathy. It will be realized that without kidney filtration the aluminum loaded compounds must be removed by suitable dialysis procedure. Further, aluminum in bone in certain cases is associated with osteoporosis and in certain forms of Alzheimer's disease there are very high concentrations of aluminum accumulated in focal areas of the cortex which can be reduced by the utilization of chelating compounds as they are described herein.

Further, specifically excluded from this invention are large molecular weight compounds where the substituted pyridine is attached to specific polymers such as a carbohydrate material which may be dextran to yield compounds that do not cross the blood brain barrier but may be excreted through kidney filtration. However, included in this invention are compounds of formula (I) containing isomeric, optically active, or racemic mixtures of substituents such as L or D amino acids and especially glucosamine.

Compositions useful for oral treatment of aluminum intoxication as defined herein for neurological disorders include incorporation of the active chelator 100–1000 mg mixed with binder and carrier substances and shaped and pressed into tablets, or mixed with inert fillers and filled into pharmaceutically approved, preferably gelatine, capsules (chaplets). A preferred tablet mixture contains 500 mg, or a lesser unit dose of active chelator selected from 2-deoxy-2-[N'-2'-methyl-3'-hydroxypyrid-4'-one]-D-glucopyranose, 2-deoxy-2-[N'-2'-ethyl-3'-hydroxypyrid-4'-one]-D-glucopyranose, 2-deoxy-2-(N-carbamoylmethyl-[N'-2'-methyl-3'-hydroxypyrid-4'-one])-D-glucopyranose, 2-deoxy-2-(N-carbamoylmethyl-[N'-2'-ethyl-3'-hydroxypyrid-4'-one])-D-glucopyranose, or 2-deoxy-2-(N'-carbamoylethyl-[N'-2'-methyl-3'-hydroxypyrid-4'-one])-D-glucopyranose.

Following are examples noting synthetic procedures of value in the preparation of the compounds of interest and intermediate compounds which are important parts of the invention but in themselves do not constitute the invention and the final products which are embodiments of the invention.

Compounds of special interest for treatment of aluminum intoxication and thus of interest in the present invention are:
1.) 2-deoxy-2-[N'-2'-methyl-3'-hydroxypyrid-4'-one]-D-glucopyranose.
2.) 2-deoxy-2-(N-carbamoylmethyl-[N'-2'-methyl-3'-hydroxypyrid-4'-one])-D- glucopyranose,
3.) 2-deoxy-2-(N-carbamoylethyl-[N'-2'-methyl-3'-hydroxypyrid-4'-one])-D- glucopyranose.

Also of interest to the invention will be adjunct treatments with compositions comprising a compound of the present invention combined with DFO and\or ascorbic acid. Instead of having one drug compound having all specific properties, it is possible to utilize two or more compounds each contributing its special property and the sum of all activities matches the desired outcome i.e. a combination or an adjunct treatment utilizing existing compounds and/or novel compounds as exemplified in the instant invention.

Selected compounds included in the present invention have been tested in vitro and in vivo and found to be effective in aluminum removal. The invention is illustrated in the examples following.

DESCRIPTION OF PREFERRED EMBODIMENTS

ANALYTICAL METHODS

Visual Spectral Analysis

A simple analytical method to detect the presence of the 3-hydroxypyrid-4-one chelating group in a compound was established. The compound was reacted with ferric iron (ferric chloride) while adjusting the pH to neutral (NaOH) to yield the iron-ligand complex. As an example, reacting the compound 2-deoxy-2-[N'-2'-methyl-3'-hydroxypyrid-4'-one])-D-glucopyranose with ferric chloride yielded the iron (III)-complex with the blue-purple solution colour characteristic of the iron(III)-3-hydroxypyrid-4-one. When 3-Hydroxy-2-methyl-4-pyrone was reacted with ferric chloride, at neutral pH, it developed an orange-red colour distinctively different from the 3-hydroxypyrid-4-one-iron (III) complexes. Thus the synthetic conversion of the pyrone (3-hydroxy-2-methyl-pyrone) starting compound to the pyridin (substituted 3-hydroxypyrid-4-one) compounds in the invention can be easily judged visually by the shift from orange/red to purple/blue of the iron (III) complexes.

Thin-Layer-Chromatography (TLC)

Silica coated TLC plates were from Kodak and the developing solution was 1:1 methanol water. Dissolved reaction products were applied as a streak with a micropipette (Hamilton) and after development dried and reacted with ferric chloride solution applied as a spray. There was immediate colour reaction of the separated bands. The reaction products usually showed relative movement of 0.2 to 0.4 rf (relative to solvent front) while the control, unreacted 3-hydroxy-2-methyl-pyrone ran at 0.7 to 0.8 rf.

High Performance Liquid Chromatography (HPLC)

A Waters HPLC system operating in reverse phase mode, utilizing a Beckman $C_{18}$ column and UV detection, was employed. The solvent mixtures usually were mixtures of water and acetonitrile. A calibration run comparing the starting material 3-hydroxy-2-methyl-pyrone to the synthetic end product 2-deoxy-2-[N'-2'-methyl-3'-hydroxypyrid-4'-one]-D-glucopyranose showed sharp widely spaced single peaks of 5.8 and 15.2 minutes elution time. The shift of the pyrone compound peak to a delayed eluting sharp peak was used to judge completion of the synthesis reaction and generation of the desired end product.

Nuclear Aluminum Removal

Utilizing isolated human neuronal nuclei preparations, the relative efficiency of intranuclear aluminum removal can be evaluated by comparing the amounts of aluminum liberated and found solvated as aluminum chelate complexes in the extra nuclear supernatant solution, the higher the extranuclear concentration the more effective is the chelator and its utility as an active component in medicinal compositions (19).

Human neuronal nuclei were isolated in ultrapure sucrose-Ca-Tris-HCl (pH 7.2) buffer. Aluminum lactate was added to suspensions of nuclei (ca 1900 ng Al+3/150 ug DNA), corresponding to about 65 aluminum ions per nucleosome, which is about 200 base pairs of DNA and reacted for 16 hours to achieve maximum Al deposition. The chelating compounds to be tested were mixed with aliquots of the nuclei suspension and allowed to react. After reaction the nuclei were pelleted by centrifugation, washed in buffer, dry ashet, the residue dissolved in ultra pure nitric acid and the Al content measured by electro-thermal atomic absorption (19).

Human Subject

The test compound was administered orally to a fully informed volunteer subject and urine was collected over a 24 hour period and combined and aliquots were prepared and analyzed for metal content.

PREPARATION OF COMPOUNDS

EXAMPLE 1

The Preparation of 1-Carboxymethyl-3-hydroxy-2-methyl-pyrid-4-one 3-hydroxy-2-methyl-4-pyrone (15 g) in methanol (250 ml) is added to an aqueous mixture (200 ml) containing glycine (7.7 g) and sodium hydroxide (10 g) with pH adjusted to 11.0, heated to 60° C. and kept with stirring under reflux conditions for 48 h. The mixture is rotary evaporated to oily residue which is made up to 100 ml with water and extracted (2×) with equal volumes of ethyl acetate. The aqueous fraction acidified with HCl to pH 1.8 to give an almost white precipitate with a yellowish hue, the desired compound. After filtration and drying the powdery compound is insoluble in water, but it is soluble in dilute base (pH 9). The mass spectrum showed a molecular ion mass $M+=186.2$ consistent with 1-carboxymethyl-3-hydroxy-2-methyl-pyrid-4-one. The compound reacts with iron to form the purple coloured iron-ligand complex indicating the presence of the 3-hydroxypyrid-4-one chelating moiety. TLC showed single a band separate and of lower rf than the 3-hydroxy-2-methyl-4-pyrone control. HPLC analysis of a mixture of 3-hydroxy-2-methyl-4-pyrone control and synthetic end product showed two sharp peaks with retention times of control=5.8 min. and sample=15.2 min.

EXAMPLE 2

The Preparation of 1-Carboxyethyl-3-hydroxy-2-methyl-pyrid-4-one 3-hydroxy-2-methyl-4-pyrone (15 g) in methanol (250 ml) is added to an aqueous mixture (200 ml) containing beta-alanine (9 g) and sodium hydroxide (10 g) with pH adjusted to 11.0. The solution is treated as described in example 1. After filtration and drying the powdery compound is insoluble in water, but it is soluble in dilute base (pH 9). The mass of the molecular ion $M+=189.2$ is consistent with 1-carboxyethyl-3-hydroxy-2-methyl-pyrid-4-one. This compound reacts with iron to form the purple coloured complex. TLC showed a single, purple band separate and of lower rf than the 3-hydroxy-2-methyl-4-pyrone control (orange red). HPLC analysis of mixture of 3-hydroxy-2-methyl-4-pyrone control and synthetic end product which showed a single sharp peaks well separated from the control.

EXAMPLE 3

The Preparation of 1-Ethoxycarbonylmethyl-3-Hydroxy-2-methyl-pyrid-4-one 3-hydroxy-2-methyl-4-pyrone (15 g) in ethanol (250 ml) has added to it glycine-ethyl ester (14 g) and concentrated aqueous sodium hydroxide to adjust pH to 10.0, the mixture is stirred at room temperature for several days, then rotary evaporated to dryness, resulting in white residue. Dissolution in acetone followed by di-ethyl ether treatment yields white precipitate of 1-ethoxycarbonylmethyl-3-Hydroxy-2-methyl-pyrid-4-one. The molecular ion mass $M+=266.7$. The compound dissolved in ethanol/water mixture with added iron forms the purple coloured complex. TLC showed a single, purple band separate and of lower rf than the 3-hydroxy-2-methyl-4-pyrone control (orange-red).

EXAMPLE 4

The Preparation of 2-deoxy-2-[N'-2'-methyl-3'-hydroxypyrid-4'-one]-D-glucopyranose 3-hydroxy-2-methyl-4-pyrone (15 g) and glucosamine hydrochloride (10.5 g) are dissolved in water/methanol 1:2 V/V (500 ml), sodium hydroxide is added (5 g) and the pH is adjusted to 11. The mixture is refluxed over night (16 h) the pH is adjusted with hydrochloric acid to 7.0 and concentrated by rotary evaporation. The residue is extracted with ethanol which after addition of di-ethyl ether yields a white precipitate. Molecular mass, $M+=324.8$, by mass spectroscopy. The compound dissolved in ethanol/water mixture with added iron forms the purple coloured complex. TLC showed a single, purple-blue band separate and of lower rf than the 3-hydroxy-2-methyl-4-pyrone control (orange-red). HPLC analysis of mixture of 3-hydroxy-2-methyl-4-pyrone control and synthetic end product which showed a single sharp peaks well separated from the control.

EXAMPLE 5

The Preparation of 2-deoxy-2-(N-carbamoylmethyl-[N'-2'-methyl-3'-hydroxypyrid-4'-one])-D-glucopyranose

[1-Carboxymethyl-3-hydroxy-2-methyl-pyrid-4-one]$_3$-Al$^{+3}$

1-Carboxymethyl-3-hydroxy-2-methyl-pyrid-4-one (9.5 g) is dissolved in 500 ml water and potassium aluminum sulphate (7.9 g) is added and stirred vigorously. The pH is raised slowly by addition of sodium hydroxide to 8.0 under constant stirring and heated to 60° C., which is continued until the pH is stable (1–2 h). The solution is dried by rotary evaporation and the residue is extracted with methanol, addition of 4 volumes of diethyl ether yields a precipitate, the tris ligand aluminum complex which is collected by filtration.

2-deoxy-2-(N-carbamoylmethyl-[N'-2'-methyl-3'-hydroxypyrid-4'-one])-D-glucopyranose (1-Carboxymethyl-3-hydroxy-2-methyl-pyrid-4-one)$_3$-AL$^{+3}$ (4.5 g) in 200 ml of dimethylformamide (DMF) has added N-hydroxysuccinimide (2.9 g] followed by addition of dicyclohexylcarbodiimide (5.2 g) dissolved in 100 ml of DMF, is stirred and left to stand over night. The reaction produces a white precipitate, N,N'-dicyclohexylurea that is filtered off and discarded. Glucosamine [5.4 g] is added to the filtrate and allowed to react for 2 h, and then the pH is adjusted to 2.5 with sulphuric acid and rotary evaporated to dryness and is then extracted with several volumes of hot methanol. The combined extracts are concentrated until precipitation begins after which the solution is stored in refrigerator over night to complete precipitation of 2-deoxy-2-(N-carbamoylmethyl-[N'-2'-methyl-3'-hydroxypyrid-4'- one])-D-glucopyranose. Molecular mass, M+=382.8, by mass spectroscopy. The compound dissolved in ethanol/water mixture with added iron forms the purple coloured complex. HPLC analysis of mixture of 3-hydroxy-2-methyl-4-pyrone control and synthetic end product which showed a single sharp peaks well separated from the control.

EXAMPLE 6

The Preparation of 2-deoxy-2-(N-carbamoylethyl-[N'-2'-methyl-3'-hydroxypyrid-4'-one])-D-glucopyranose 2-deoxy-2-(N-carbamoylethyl-[N'-2'-methyl-3'-hydroxypyrid-4'-one])-D-glucopyranose is synthesized by the method of example 5 substituting 1-carboxyethyl-3-hydroxy-2-methylpyrid-4-one generated according to example 2 for 1-carboxymethyl-3-hydroxy-2-methylpyrid-4-one in example 1 above with substituting glycine by beta alanine.

Compounds given in examples 4 and 5 respectively are of prime interest for treatment procedures especially aluminum removal in selected forms of (sporadic, non-familial) Alzheimer's disease. The compound 2-deoxy-2-(N-carbamoylethyl-[N'-2'-methyl-3'-hydroxypyrid-4'-one])-D-glucopyranose also being useful for said purpose but of lesser interest.

BIOLOGICAL RESULTS

EXAMPLE 7

The Al-chelator 2-deoxy-2-[N'-2'-methyl-3'-hydroxypyrid-4'-one]-D-glucopyranose was tested for its ability to remove nuclear bound aluminum. The chelators to be tested were incubated in aliquots of neuronal nuclei suspension and processed according to the method above (Nuclear aluminum removal). Compounds tested for aluminum removal efficiency were: DFO (10 mM), DFO (10 mM) plus ascorbic acid (100 mM) and the selected chelator 2-deoxy-2-[N'-2'-methyl-3'-hydroxypyrid-4'-one]-D-glucopyranose (10 mM) as an example of the invention. Post chelation nuclear Al retention was 84% for the DFO treatment and 75% for, 2-deoxy-2-[N'-2'-methyl-3'-hydroxypyrid-4'-one]-D-glucopyranose. Interestingly, a combination treatment with DFO+Ascorbic acid resulted in retention of 65%. The results show that at the chelate concentration selected, a combination treatment with DFO+ascorbic acid would be the most effective way to remove nuclear Al. However, a treatment with the chelator 2-deoxy-2-[N'-2'-methyl-3'-hydroxypyrid-4'-one]-D-glucopyranose alone is comparable. Neuronal nuclei are one of the body compartments where aluminum toxicity is expressed (Alzheimer's disease (3)).

EXAMPLE 8

To be particularly useful as an in vivo chelating agent the modified 3-hydroxypyrid-4-one-glucose compounds must enter the blood stream preferably via oral administration and exit the body preferably via urinary excretion as a metal (iron or aluminum) complex.

To a fully informed healthy middle aged human being as a test subject was administered orally 250 mg of the compound 2-deoxy-2-[N'-2'-methyl-3'-hydroxypyrid-4'-one]-D-glucopyranose. No adverse effects were noted. Starting after administration of the compound, urine samples were collected for a 24 hour period and combined. Aliquots of the 24 hour combined urine sample were analyzed for iron content. The iron content of pre-treatment urine samples were used as standards for comparison. Analysis showed that excretion when compared to pre-treatment was increased by a factor of 3 showing the compound can enter the blood stream and be active in metal (iron) removal. Noting, aluminum removal occurs only after all available iron is removed.

PREPARATION OF MEDICAMENTS

Sample Preparations are Formulated as Follows

EXAMPLE 9

To produce the high dose tablet of 2-deoxy-2-[N'-2'-methyl-3'-hydroxypyrid-4'-one]-D-glucopyranose, 500 mg of active chelator compound (crystalline powder) are mixed with 200 mg pharmaceutical grade microcrystalline starch, 40 mg of magnesium stearate, and 10 mg of sucrose, thoroughly mixed and pressed into 750 mg tablets.

EXAMPLE 10

Lower dose tablets are fashioned from 250 mg active chelator mixed with 200 mg pharmaceutical grade microcrystalline starch, 40 mg magnesium stearate, and 10 mg of sucrose, thoroughly mixed and pressed into 500 mg tablets.

EXAMPLE 11

To produce the high dose tablet of 2-deoxy-2-(N-carbamoylmethyl-[N'-2'-methyl-3'-hydroxypyrid-4'-one])-D-glucopyranose, 500 mg of active chelator compound (crystalline powder) are mixed with 200 mg pharmaceutical grade microcrystalline starch, 40 mg of magnesium stearate, and 10 mg of sucrose, thoroughly mixed and pressed into 750 mg tablets.

EXAMPLE 12

Lower dose tablets are fashioned from 250 mg active chelator mixed with 200 mg pharmaceutical grade microcrystalline starch, 40 mg magnesium stearate, and 10 mg of sucrose, thoroughly mixed and pressed into 500 mg tablets.

EXAMPLE 13

To produce the high dose tablet of 2-deoxy-2-(N-carbamoylethyl-[N'-2'-methyl-3'-hydroxypyrid-4'-one])-D-glucopyranose, 500 mg of active chelator compound (crystalline powder) are mixed with 200 mg pharmaceutical grade microcrystalline starch, 40 mg of magnesium stearate, and 10 mg of sucrose, thoroughly mixed and pressed into 750 mg tablets.

EXAMPLE 14

Lower dose tablets are fashioned from 250 mg active chelator mixed with 200 mg pharmaceutical grade microcrystalline starch, 40 mg magnesium stearate, and 10 mg of sucrose, thoroughly mixed and pressed into 500 mg tablets.

I claim:
1. A 2-deoxy-2-[N'-2'-alkyl-3'-hydroxypyrid-4'-one]-D-glucopyranose of the general formula:

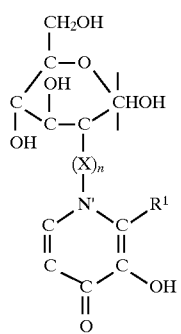

where $x_n$ is —NHCO(CH$_2$)$_m$CHR$^2$— and m and n are 0 or 1; and R$^1$ is selected from methyl or ethyl, and R$^2$ is selected from hydrogen, CH$_3$—, (CH$_3$)$_2$CH—, (CH$_3$)$_2$CHCH$_2$—, CH$_3$CH$_2$CH(CH$_3$)—, CH$_3$SCH$_2$CH$_2$—, C$_6$H$_5$—CH$_2$—, HOCH$_2$—, CH$_3$CH(OH)—, HSCH$_2$—, HO—C$_6$H$_4$—CH$_2$—, H$_2$NCOCH$_2$—, H$_2$NCOCH$_2$CH$_2$—, HOCOCH$_2$—, HOCOCH$_2$CH$_2$—, H$_2$NCH$_2$CH$_2$CH$_2$CH$_2$—, H$_2$NC(NH)NHCH$_2$CH$_2$CH$_2$—,

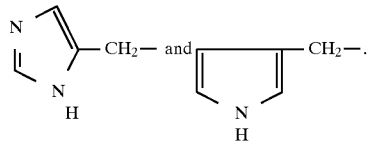

2. A compound as defined in claim 1 being 2-deoxy-2-[N'-2'-methyl-3'-hydroxypyrid-4'-one]-D-glucopyranose.

3. A compound as defined in claim 1 being 2-deoxy-2-[N'-2'-ethyl-3'-hydroxypyrid-4'-one]-D-glucopyranose.

4. A compound as defined in claim 1 being 2-deoxy-2-(N'-carbamoylmethyl-[N-2'-methyl-3'-hydroxypyrid-4'-one])-D-glucopyranose.

5. A compound as defined in claim 1 being 2-deoxy-2-(N'-carbamoylmethyl-[N-2'-ethyl-3'-hydroxypyrid-4'-one])-D-glucopyranose.

6. A compound as defined in claim 1 being 2-deoxy-2-(N'-carbamoylethyl-[N-2'-ethyl-3'-hydroxypyrid-4'-one])-D-glucopyranose.

7. A pharmaceutical composition comprising a 2-deoxy-2-[N'-2'-alkyl-3'-hydroxypyrid-4'-one]-D-glucopyranose of the general formula:

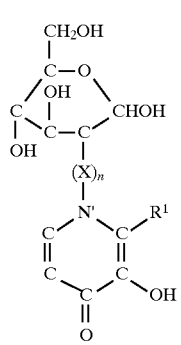

where $x_n$ is —NHCO(CH$_2$)$_m$CHR$^2$— and n and m are 0 or 1; and R$^1$ is selected from methyl or ethyl, and R$^2$ is selected from hydrogen, CH$_3$—, (CH$_3$)$_2$CH—, (CH$_3$)$_2$CHCH$_2$—, CH$_3$CH$_2$CH(CH$_3$)—, CH$_3$SCH$_2$CH$_2$—, C$_6$H$_5$—CH$_2$—, HOCH$_2$—, CH$_3$CH(OH)—, HSCH$_2$—, HO—C$_6$H$_4$—CH$_2$—, H$_2$NCOCH$_2$—, H$_2$NCOCH$_2$CH$_2$—, HOCOCH$_2$—, HOCOCH$_2$CH$_2$—, H$_2$NCH$_2$CH$_2$CH$_2$CH$_2$—, H$_2$NC(NH)NHCH$_2$CH$_2$CH$_2$—,

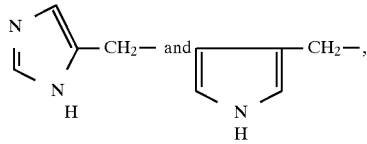

or physiologically acceptable salt thereof in admixture with a pharmaceutically acceptable diluent or carrier.

8. A pharmaceutical composition according to claim 7 comprising a compound selected from the group consisting of 2-deoxy-2-[N'-2'-methyl-3'-hydroxypyrid-4'-one]-D-glucopyranose; 2-deoxy-2-[N'-2'-ethyl-3'-hydroxypyrid-4'-one]-D-glucopyranose; 2-deoxy-2-(N-carbamoylmethyl-[N'-2'-methyl-3'-hydroxypyrid-4'-one])-D-glucopyranose; 2-deoxy-2-(N-carbamoylmethyl-[N'-2'-ethyl-3'-hydroxypyrid-4'-one])-D-glucopyranose; 2-deoxy-2-(N-carbamoylethyl-[N-2'-methyl-3'-hydroxypyrid-4'-one])-D-glucopyranose.

9. A method for the removal of metal ions selected from the group consisting of aluminum (III) iron (II) and iron (III) from the body of a patient, said method comprising administering to said patient an effective amount of a 2-deoxy-2-[N'-2'-alkyl-3-hydroxypyrid-4-one]-D-glucopyranose of the general formula,

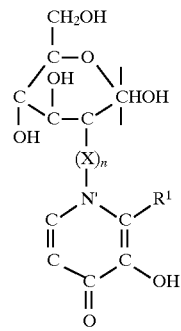

where $x_n$ is —NHCO(CH$_2$)$_m$CHR$^2$— and n and m are 0 or 1; and R$^1$ is selected from methyl or ethyl, and R$^2$ is selected from hydrogen, CH$_3$—, (CH$_3$)$_2$CH—, (CH$_3$)$_2$CHCH$_2$—, CH$_3$CH$_2$CH(CH$_3$)—, CH$_3$SCH$_2$CH$_2$—, C$_6$H$_5$—CH$_2$—, HOCH$_2$—, CH$_3$CH(OH)—, HSCH$_2$—, HO—C$_6$H$_4$—CH$_2$—, H$_2$NCOCH$_2$—, H$_2$NCOCH$_2$CH$_2$—, HOCOCH$_2$—, HOCOCH$_2$CH$_2$—, H$_2$NCH$_2$CH$_2$CH$_2$CH$_2$—, H$_2$NC(NH)NHCH$_2$CH$_2$CH$_2$—,

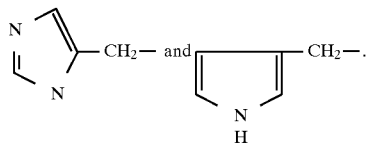

10. A method as defined in claim 9 wherein m=0, n=0 and R$^1$ is a methyl group.

11. A method as defined in claim 9 wherein m=0, n=0 and R$^1$ is an ethyl group.

12. A method as defined in claim 9 wherein m=0, n=1 and R$^1$ is a methyl group and R$^2$ is hydrogen.

13. A method as defined in claim 9 wherein m=0, n=1 and R$^1$ is an ethyl group and R$^2$ is hydrogen.

14. A method as defined in claim 9 wherein m=1, n=1 and R$^1$ is a methyl group and R$^2$ is hydrogen.

15. A method according to claim 9, where the metal ion is iron (II) or iron (III).

16. A method according to claim 9, where the metal ion is aluminum (III).

17. A method according to claim 9, where the metal ion is iron (II) or iron (III) and the active chelating compound is selected from the group consisting of 2-deoxy-2-[N'-2'-methyl-3'-hydroxypyrid-4'-one]-D-glucopyranose; 2-deoxy-2-[N'-2'-ethyl-3'-hydroxypyrid-4'-one]-D-glucopyranose; 2-deoxy-2-(N-carbamoylmethyl-[N'-2'-methyl-3'-hydroxypyrid-4'-one])-D-glucopyranose; 2-deoxy-2-(N-carbamoylmethyl-[N'-2'-ethyl-3'-hydroxypyrid-4'-one])-D-glucopyranose or 2-deoxy-2-(N-carbamoylethyl-[N'-2'-methyl-3'-hydroxypyrid-4'-one])-D-glucopyranose.

18. A method according to claim 9, where the metal ion is aluminum (III) and the active chelating compound is selected from the group consisting of 2-deoxy-2-[N'-2'-methyl-3'-hydroxypyrid-4'-one]-D-glucopyranose; 2-deoxy-2-[N'-2'-ethyl-3'-hydroxypyrid-4'-one]-D-glucopyranose; 2-deoxy-2-(N-carbamoylmethyl-[N'-2'-methyl-3'-hydroxypyrid-4'-one])-D-glucopyranose; 2-deoxy-2-(N-carbamoylmethyl-[N'-2'-ethyl-3'-hydroxypyrid-4'-one])-D-glucopyranose or 2-deoxy-2-(N-carbamoylethyl-[N'-2'-methyl-3'-hydroxypyrid-4'-one])-D-glucopyranose.

19. A method according to claim 18 for the treatment of a patient in need of said treatment having toxic amounts of aluminum or iron, or alternatively having toxic amounts of both, aluminum and iron in the body and especially in neuronal cells which comprises administering to said patient therapeutically effective amounts of the compound and providing an adjunct treatment comprising simultaneous administration of therapeutically active amounts of ascorbic acid.

* * * * *